(12) United States Patent
Fuchs et al.

(10) Patent No.: US 8,679,555 B2
(45) Date of Patent: Mar. 25, 2014

(54) METHOD FOR PRODUCING ORGANICALLY-BOUND VITAMIN B

(75) Inventors: Norbert Fuchs, Mariapfarr (AT); Rupert Loidl, Mariapfarr (AT); Behzad Sadeghi, Vienna (AT)

(73) Assignee: JHS-Privatstiftung, Bruck a.d. Mur (AT)

( * ) Notice: Subject to any disclaimer, the term of this patent is extended or adjusted under 35 U.S.C. 154(b) by 1333 days.

(21) Appl. No.: 11/763,974

(22) Filed: Jun. 15, 2007

(65) Prior Publication Data

US 2007/0292541 A1    Dec. 20, 2007

(30) Foreign Application Priority Data

Jun. 16, 2006   (AT) .................................. 1029/2006

(51) Int. Cl.
*A61K 36/89* (2006.01)
*A61K 36/42* (2006.01)
*A61K 36/05* (2006.01)
*A61K 36/00* (2006.01)
*C12N 5/00* (2006.01)
*C12N 5/02* (2006.01)

(52) U.S. Cl.
USPC ........... 424/750; 424/725; 424/758; 424/768; 424/776; 435/430; 435/431

(58) Field of Classification Search
None
See application file for complete search history.

(56) References Cited

U.S. PATENT DOCUMENTS

| | | | | |
|---|---|---|---|---|
| 5,153,001 A | * | 10/1992 | Ismail | 424/455 |
| 5,973,224 A | | 10/1999 | Fuchs et al. | 424/736 |
| 2003/0139296 A1 | * | 7/2003 | Lee et al. | 504/239 |
| 2003/0233673 A1 | * | 12/2003 | Sato | 800/278 |
| 2004/0063582 A1 | | 4/2004 | Johnson | 504/241 |
| 2004/0115288 A1 | * | 6/2004 | Sadeghi et al. | 424/750 |

FOREIGN PATENT DOCUMENTS

| | | | |
|---|---|---|---|
| EP | 1371283 | | 12/2003 |
| GB | 484981 | | 5/1938 |
| GB | 485097 | | 5/1938 |
| GB | 500284 | | 2/1939 |
| GB | 1108164 | | 4/1968 |
| JP | 2004065240 | * | 3/2004 |
| JP | 2006246891 | * | 9/2006 |
| WO | WO 99/26470 | | 6/1999 |
| WO | WO 00/13502 | | 3/2000 |
| WO | WO 2005/063002 | | 7/2005 |

OTHER PUBLICATIONS

Lintschinger et al. Uptake of Various Trace Elements During Germination of Wheat, Buckwheat and Quinoa. Plants Foods for Human Nutrition. 50. pp. 223-237. 1997.*
Hashimi et al. Vitamin B, Relative Nutritive Value and Palatability of Germinated Corn (Zea Mays L.) Pertanika 2(2). pp. 128-132. 1979.*
Mozafar et al. Uptake and Transport of Thiamin (Vitamin B1) by Barley and Soybean. J. Plant Physiol. vol. 139. pp. 436-446. 1992.*
Quinoa. Retrieved from the internet <http://webarchive.org/web/20040717034337/http://www.vurv.cz/altercrop/quinoa.html>. Retrieved on Feb. 19, 2009. Web archive date 2004. pp. 1-4.*
European Search Report, issued in European Patent Application No. 07450110.7, dated Oct. 16, 2007.
Mozafar and Oertli, "Uptake and Transport of Thiamin (Vitamin B1) by Barley and Soybean," *J. Plant Physiol.*, 139:439-442, 1992.
Mozafar et al., "Uptake of microbially-produced vitamin (B12) by soybean", *Plant Soil*, 139:23-30, 1992.
Office Communication issued in Canadian Patent Application No. 2,591,055, dated Jun. 13, 2013.

* cited by examiner

*Primary Examiner* — Chris R Tate
(74) *Attorney, Agent, or Firm* — Fulbright & Jaworski LLP

(57) ABSTRACT

The present invention relates to a method for producing organically-bound vitamin B, preferably vitamin B1, B2, B3, B5, B6, B7, B9, B12, or mixtures thereof, in plants, wherein plant seeds are soaked in the solution of the respective vitamin and are cultured to vitamin-B-enriched germ buds by subsequent sprinkling.

28 Claims, No Drawings

METHOD FOR PRODUCING ORGANICALLY-BOUND VITAMIN B

BACKGROUND OF THE INVENTION

The present invention relates to the enrichment and modification of vitamins in plant food stuffs.

1. Field of the Invention

Vitamins are organic compounds required in small amounts for a plurality of chemical functions. The human organism cannot develop vitamins at all or only in an insufficient amount and, thus, they have to be supplied via food intake. As co-factors or prosthetic groups of cellular enzymes active vitamins have, in particular, catalytic functions: as bio-catalysts they allow for metabolic reactions under physiological conditions, which reactions would—without their catalytic influence—only be possible under high pressure or high temperatures. While human beings and animals cannot or only to a restricted extent produce vitamins endogenously, plants and "lower" organisms (e.g. bacteria and/or algae) are capable of building said biocatalysts from suitable carbon, nitrogen, mineral and natural energy sources (sun light) in a biochemical way. Consequently, the human being is reliant on the regular and sufficient supply of vitamins to maintain smooth energy metabolism, anabolism and functional metabolism of his organism. Thus, all growth, defense and regeneration processes of the human organism depend on sufficient supplies of vitamins in the body.

Vitamin preparations are used in an attempt to directly increase vitamin contents of food. For example, the vitamin level of a food is complemented by admixing vitamin preparations. For this purpose, plants or plant products can be sprinkled with vitamin preparations.

2. Description of Related Art

US 2004/0115288 A1 describes an alternative way for increasing the vitamin content. The vitamin-B content in plants is increased in a natural manner by a controlled procedure of plant cuttings, alternated with defined growth phases.

U.S. Pat. No. 5,973,224 discloses a method for generally increasing the nutrient content in plants, wherein plant embryos are incubated in selected electrolyte solutions.

GB 500 284, GB 485 097 and GB 484 981 relate to the treatment of plant seeds with growth-promoting substances, including vitamin B1, lactoflavin (vitamin B2) and biotin (vitamin B7).

An advantage of vitamin treatment is that plant growth can be accelerated, thus raising output. EP 524 411 A1 suggests to treat plant seeds with a vitamin-B1 composition (vitamin B1 is also referred to as thiamine or aneurine), optionally with a fungicide.

EP 1 371 283 A2 describes soaking of plant seeds in a vitamin-B12 solution to increase the vitamin-B12 content of the plants. Plants do not produce vitamin B12 themselves but absorb it from the soil (where it is produced by bacteria). In this document vitamin B12 refers to all forms of vitamin B12, i.e. cobalamin, cyanocobalamin, hydroxycobalamin, methylcobalamin and adenosylcobalamin. The vitamin B12 need of a human being is relatively low, namely 1 µg, the content thereof in plants being just as low. This vitamin can be enriched in plants up to 0.5 µg/g by plant-seed treatment.

WO 2000/013502 A1 relates to a fertilizer to be applied on leaves, e.g. by sprinkling.

US 2004/0063582 A1 relates to seed materials with adhering micronutrients, vitamins and pesticides.

WO 1999/026470 A1 concerns a culture medium for plants, in which plant seeds may be cultured.

GB 1 108 164 describes a nutrient solution, in which seeds can be germinated for faster growth.

WO 2005/063002 A1 relates to artificial somatic embryogenesis in cotton plants in a nutrient solution.

The knowledge that a regular and sufficient vitamin supply is essential for animals and human beings has led to chemical, biochemical and fermentative development and production of isolated vitamins on an industrial scale in the last decades. Supplying animals and human beings with thus obtained vitamins has turned out to be necessary and reasonable in most cases and many large-scale intervention studies have been conducted, in particular in the last 10 years, showing that the supply of single, isolated and high-dosed vitamins may also have negative effects under certain circumstances and in several population groups:

Two large-scale Scandinavian studies have shown that the supply of isolated beta carotene increases the lung cancer death rates of smokers and asbestos workers (ATBC study and CARET study).

A further double-blind study conducted with 4,000 diabetics and/or persons suffering from cardiovascular diseases has shown that the supply of isolated vitamin E increases the risk of cardiac complications in the verum group (HOPE study).

A recently presented Norwegian study conducted with 3,800 heart attack patients has shown that the regular intake of a combination of synthetic vitamin B6, vitamin B12 and folic acid increased the risk of heart attacks or strokes by 20% in the verum group as compared to the placebo group (NORVIT study).

SUMMARY OF THE INVENTION

Thus, it is an object of the present invention to provide vitamins in sufficient amounts which are compatible with the consumers or are more compatible, as well as to obtain biologically active vitamin-B complexes in organically bound form with high bioavailability.

According to the invention this object is achieved by providing plants with high vitamin contents, which plants have been soaked in a vitamin solution in their seed stage. Subject matter of the present invention is a method for producing organically-bound vitamin B, preferably selected from vitamin B1, B2, B3, B5, B6, B7, B9, B12, or mixtures thereof, in plants, wherein germinative plant seeds are at first soaked in a solution of the respective vitamin or vitamin mixture and are sprinkled with the respective vitamin solutions during germination process. "Germination" means the growth which starts after the resting phase of the plant seed. The germ bud ("seedling") grows out of the seed. Then, the germinative plant seeds are soaked and steeped (caused to begin to germinate) and subsequently, are prompted to germinate by sprinkling. The germination can be considered completed when the body of the plant seed has been used up and, optionally, the non-utilizable shell of the seed (when present) has been dropped. The germ bud is cultured to vitamin-B-enriched plant germ buds by subsequent sprinkling.

Preferably, the vitamin is selected from B3, B5, B6 or B9. The initial soaking (steeping) lasts until swelling can be observed. After steeping, the germ bud is cultured and sprinkled with the vitamin solution so that germination and growth is effected. The germ bud can be sprinkled once or several times the day. It is sprinkled until germination is observable, e.g. depending on the type of plant, 1 to 20 days, in particular more than 1, 2, 3, 4, 5, 6, 7 or 8 days and, optionally, less than 30, 25, 20, 18, 15, 12, 10, 8, 7, 5 or 3 days. After soaking or after germination has started, it may be sprinkled over a period of up to or at least 20, 22, 24, 26, 28, 30, 32, 34, 36, 38, 40, 42, 44, 45, 46, 48, 50, 52, 54, 56, 58, 60, 62, 64, 66, 68, 70, 75, 80, 85, 90, 95, 100, 105, 110, 115, 120, 130, 140, 150 or 160 hours. As plants are treated over a relatively short period of time, they can be kept free of plant protection agents, such as, e.g. pesticides and fungicides, in preferred embodiments.

In contrast to exemplarily indicated studies on vitamin preparations, showing possible negative effects provoked by long-term supply of synthetic single vitamins or vitamin combinations, there is worldwide no study showing negative effects caused by regular supply of natural, biologically active plant vitamins.

One reason for the discrepancy in the biological effect of synthetic and naturally grown vitamins may be that natural vitamins occur mostly bound and complex in the plant environment, whereas synthetic vitamins are chemically unbound, isolated and clearly defined molecular compounds.

(Synthetic) aneurine (as free base or as salt) is not present in edible plants in this form and can only be isolated as biologically active thiamine pyrophosphate or thiamine triphosphate.

Vitamin B2 is synthetically defined as riboflavin, whereas it is present in the plant organism primarily in a great number of so-called flavoproteins, as FADH or, e.g., also as FMN in its biologically active form.

Vitamin B3 is, when chemically produced, in turn, a nicotinic acid (niacine) or nicotinic acid amide, whereas the plant, biologically active form of vitamin B 3 mainly occurs as NAHD and NADPH (in reduced form) and/or as NAD and NADP (in its oxidized form).

Synthetic pantothenic acid (vitamin B5) does, in turn, practically not occur in free form in the plant organism, but unfolds its biological function as biologically active co-enzyme A there.

Vitamin B6 can be synthesized in the laboratory as pyridoxol, pyridoxal and pyridoxamine, whereas the (plant) biologically active form primarily occurs as pyridoxal phosphate.

In plants, synthetic biotin (vitamin B7) is, in turn, present primarily as biological biocytin.

Chemically defined folic acid (vitamin B9), in turn, occurs in the plant organism in the form of the most different folate molecules, e.g. pteroyldiglutamate, pteroyloligoglutamate and pteroylpolyglutamate.

Vitamin B12, in turn, is generally not present in plant cells, it is, however, present in microorganisms, e.g. as methylcobalamin, cyanocobalamin and adenosylcobalamin.

Thus, according to the invention under "organically bound vitamin B" (or organic vitamin-B form—"phyto vitamins" or "phytamines") a vitamin-B derivative, complex or variant is to be understood, which differs from the synthetically produceable vitamins in that it occurs in plants and/or is a mixture of compounds falling under the respective vitamin-B category (B1, B2, etc.). "Organically bound" is not to be understood as "organical-chemically bound", but relates to the naturally biologically occurring forms of B-vitamins. The inventive method can be used for producing organically bound vitamin B, said production optionally not including any synthetically produceable vitamins, or for partially or completely converting synthetically vitamins into their natural biological forms. Preferably, the method is conducted up to a portion of the respective organically bound vitamin B relative to the whole vitamin-B content of the respective vitamin (e.g. vitamin B1, B2, B3, B5, B6, B7, B9 or B12) of at least 0.1%, 0.5%, 1%, 2%, 3%, 4%, 5%, 6%, 7%, 8%, 9%, 10%, 15%, 20%, 30% or 40%, or products with these portions are provided.

Whereas natural vitamin complexes for vitamin C (e.g. from acerola, hibiscus or dog rose fruits), for vitamin E (e.g. from soya or rice germs) as well as for carotinoides (e.g. from carrots, algae or palm-oil) have already been known, at present, there is worldwide no natural source worth mentioning for the vitamins of the B-group, apart from yeast or liver extracts.

Thus, according to the invention, a vitamin-B variant is preferably provided selected from thiamine pyrophosphate, thiamine triphosphate, FAD (flavin adenine dinucleotide), FADH, FADH2 (reduced forms of FAD), FMN (flavin mononucleotide), NADH, NADHP, NAD or NADP, co-enzyme A, pyridoxyl phosphate and biocytin, pteroyldiglutamate, pteroyloligoglutamate and pteroylpolyglutamate, and the method for enrichment of plants with these vitamins is provided.

Preferably, the plant seeds are germinated in the solution of the respective vitamin. Preferably, the plant seeds are pregerminated by soaking and are subsequently left to germinate after regular sprinkling. Absorption of vitamin B is particularly efficient in the first growth cycles.

Preferably, the plant seeds are soaked for 1 h to 24 or 48 hours, preferably 10, 14, 16, 20, 24, 30, 36 or 48 hours at the most and at least 30 min, in particular 1, 2, 3 or 4 hours.

In special embodiments the mass ratio of the plant seeds to the solution of the respective vitamin is between 1:1 to 1:20, preferably up to 1:10, mostly preferred up to 1:5. In particular, the amount of the vitamin in the solution of the respective vitamin relative to 100 g of plant seeds to be treated is larger than 0.01 mg, preferably larger than 0.1 mg, more preferably larger than 1 mg, mostly preferred larger than 10 mg, and smaller than 20 g, preferably smaller than 5 g, mostly preferred smaller than 1 g.

In preferred embodiments the plant is cultured and sprinkled preferably with a vitamin-B solution to increase vitamin absorption. In particular, it is sprinkled over several days so that germination is completed, i.e. the seed is used up.

Then, the plants are purified from the adhering vitamin in order to not remove the vitamin which has been converted in the organic form. In other embodiments the plant seeds are prevented from germinating by, e.g. drying, or the germ buds are harvested directly after germination, e.g. after the plants have grown up to 0.5 cm, 1 cm, 2 cm or 3 cm—and, in particular, after the plant seed has been used up.

Preferably, the organically bound vitamin B is then isolated. This can be done in a conventional way, such as by reducing the plant to small pieces, extraction or recrystallization. Optionally, the vitamin can also be purified, this can also be done in a conventional way, such as, e.g. crystallization or chromatography.

Preferably, the plant seed is selected from plant, edible and germinative kinds of seeds, in particular grass, vegetable and cereal seeds.

The germinative seeds are preferably selected from azuki beans, aramanth, lucerne (Alphalpha), picris (cress), sorts of beans, watercress, buckwheat, sorts of peas, fenugreek, soya, barley, oat, millet, pumpkin, chickpea, sorts of cabbage, sorts of lentils, sorts of linseeds, corn, rice, radish, rye, sesame, mustard, sun flowers, wheat and quinoa.

The plant germ buds enriched with vitamin B serve as biologically high-quality raw material, preferably as basis for food supplements, dietary preparations, functional food and veterinary products, in solid, semi-solid or liquid form, optionally also in gastric-juice-resistant form.

DESCRIPTION OF ILLUSTRATIVE EMBODIMENTS

The present invention is explained in more detail by the following examples, yet without being restricted thereto.

EXAMPLES

The aim of the examinations was to selectively introduce chemically defined compounds of vitamins from the B group into plant organisms and to convert them into biologically active compounds. Germinative, edible plant seeds were particularly suitable as plant enrichment agents. Edible germ buds from cereals and other plant seeds are considered particularly valuable according to current findings in nutrition research. They impress by a better protein quality as compared to non-germinated seeds, by a content pattern of polyunsaturated fatty acids of higher quality, but primarily by a better bioavailability of the vitamins, mineral substances and trace elements contained. The aim of the tests was to selectively enrich germinative seeds with vitamins of the B complex by enrichment via standardized nutrient solutions, in order to obtain germ buds with high contents above average of biologically active vitamins of the B complex, yet, at the same time, also obtaining standardized contents thereof.

Example 1

Pre-Tests

In order to examine the basic absorbency of different edible germ buds for B vitamins, standardized aqueous solutions of niacine and/or cobalamin were added to germinative wheat, buckwheat and quinoa seeds. This was done in the following way:

Step 1: 100 g seeds (wheat, buckwheat, quinoa) each were prewashed with double-distilled water.

Step 2: 100 g of the pre-washed seed type each were steeped in the respective vitamin nutrient solution:
  wheat for 12 hours
  buckwheat for 16 hours
  quinoa for 1 hour The amounts of the respective steeping-nutrient solution were 500 ml each.

Step 3: After the predetermined steeping time in the vitamin-nutrient solutions, the pre-germinated seeds were filtered by means of a filter and pre-germinated for over 12 hours at room temperature.

Step 4: Each single sample was sprinkled with 25 ml freshly produced vitamin-nutrient solution once a day for 4 days.

Step 5: After 96 hours (4 days) germination duration, the germ buds were washed 3× with 800 ml double-distilled water each, in order to completely remove the vitamin traces adhering to the surface. Then, the samples were dried for 10 hours in the drying chamber at 70 degree Celsius.

The following Table 1 indicates the vitamin concentrations of the niacine and cobalamin nutrient solutions:

TABLE 1

| Standards | Conc. 1 [g/L] | Conc. 2 [g/L] | Conc. 3 [g/L] | Conc. 4 [g/L] | Conc. 5 [g/L] | Conc. 6 [g/L] |
|---|---|---|---|---|---|---|
| Niacine | 0.1 | 0.5 | 1 | 2 | 5 | 10 |
| Cobalamin | 0.001 | 0.005 | 0.01 | 0.02 | 0.05 | 0.1 |

Example 2

Gradual Increase of Vitamins

The following Table 2 indicates the niacine contents in mg/100 g dried germ bud.

W(0), B(0), Q(0) refer to non-germinated wheat, buckwheat and quinoa. W(zdw), B(zdw), Q(zdw) refer to the respective kinds of germ buds which have been germinated according to the same method as the test germ buds, yet not in vitamin-containing nutrient solutions but in double-distilled water.

The denotations (Conc.1) to (Conc.6) symbolize the respective niacine concentrations of the nutrient solutions, in which the respective seeds have been germinated.

TABLE 2

| Samples | B3 [mg/100 g germ bud] | Samples | B3 [mg/100 g germ bud] | Samples | B3 [mg/100 g germ bud] |
|---|---|---|---|---|---|
| W (0) | 4.1 | B (0) | 5.2 | Q (0) | 1.6 |
| W (zdw) | 5.4 | B (zdw) | 6.2 | Q (zdw) | 3.1 |
| W (Conc. 1) | 7.9 | B (Conc. 1) | 8 | Q (Conc. 1) | 3.9 |
| W (Conc. 2) | 17.5 | B (Conc. 2) | 35.5 | Q (Conc. 2) | 19.5 |
| W (Conc. 3) | 74 | B (Conc. 3) | 70.3 | Q (Conc. 3) | 35.5 |
| W (Conc. 4) | 195 | B (Conc. 4) | 186 | Q (Conc. 4) | 175 |
| W (Conc. 5) | 400 | B (Conc. 5) | 791 | Q (Conc. 5) | 626 |
| W (Conc. 6) | 729 | B (Conc. 6) | 1680 | Q (Conc. 6) | 1240 |

Table 3 indicates—in analogous symbolism—the value of contents and enrichment for vitamin B12:

TABLE 3

| Samples | B12 [mg/100 g germ bud] | Samples | B12 [mg/100 g germ bud] | Samples | B12 [mg/100 g germ bud] |
|---|---|---|---|---|---|
| W (0) | 4.8 | B (0) | 0.9 | Q (0) | 1.4 |
| W (zdw) | 74.7 | B (zdw) | 12.3 | Q (zdw) | 23.8 |
| W (Conc. 1) | 90 | B (Conc. 1) | 111 | Q (Conc. 1) | 69 |
| W (Conc. 2) | 349 | B (Conc. 2) | 481 | Q (Conc. 2) | 378 |
| W (Conc. 3) | 658 | B (Conc. 3) | 895 | Q (Conc. 3) | 676 |
| W (Conc. 4) | 580 | B (Conc. 4) | 700 | Q (Conc. 4) | 570 |
| W (Conc. 5) | 3240 | B (Conc. 5) | 1460 | Q (Conc. 5) | 1580 |
| W (Conc. 6) | 4170 | B (Conc. 6) | 3010 | Q (Conc. 6) | 2360 |

The detection of the individual vitamin contents was done by Institut Kuhlmann, Hedwig-Laudien-Ring 3, D-67061 Ludwigshafen, according to the following analysis method:

Vitamin B1 microbiologically with Hanseniaspora uvarum

Vitamin B2 microbiologically with Lactobacillus rhamnosus (AOAC 940.33)

Vitamin B6 microbiologically with Lactobacillus sitophila

Vitamin B12 microbiologically with Lactobacillus delbrüfckii (AOAC 952.20)

Niacine microbiologically with Lactobacillus plantarum (AOAC 944, 13)

Folic acid microbiologically with Enteroroccus hirae (AOAC 944, 12)

Pantothenic acid microbiologically with Lactobacillus plantarum (AOAC 945, 74)

Biotin microbiologically with Neurospora crassa

Example 3

Complex Vitamin Compositions

After the pretests with the above-indicated 3 seed types had gone positively, the quinoa-seeds were caused to germinate according to a method with a complex vitamin-B nutrient solution of the following composition (Table 4): Vitamin content in 1 liter aqueous nutrient solution:

| Vitamins | mg/liter |
|---|---|
| Vitamin B1 (thiamine) | 1,500 |
| Vitamin B2 (riboflavin) | 10,000 |
| Vitamin B3 (niacine) | 22,000 |
| Vitamin B5 (pantothenic acid) | 25,000 |
| Vitamin B6 (pyridoxin) | 3,300 |
| Vitamin B7 (biotin) | 250 |
| Vitamin B9 (folic acid) | 1,000 |
| Vitamin B12, cyanocobalamin | 5 |

The quinoa germing buds obtained after washing, germination and drying according to the above-illustrated method had the following vitamin contents:

| Vitamins | mg/100 g |
|---|---|
| Vitamin B1 (thiamine) | 83.4 |
| Vitamin B2 (riboflavin) | 134.0 |
| Vitamin B3 (niacine) | 1300.0 |
| Vitamin B5 (Pantothenic acid) | 793.0 |
| Vitamin B6 (pyridoxine) | 155.0 |
| Vitamin B7 (biotin) | 14.9 |
| Vitamin B9 (folic acid) | 12.4 |
| Vitamin B12, cyanocobalamin | 0.21 |

Example 4

Converting of the Vitamins

In a further method step it has been examined whether, depending on the duration of germination, a part of the vitamin absorbed during steeping from the steeping-soaking solution is converted into organically bound forms during the germination process. To this end, 200 g germinative quinoa seeds were soaked for 6 hours in 320 ml nutrient solution of the following composition:
Vitamins dissolved in 1 l water:

| Vitamins | mg/l water |
|---|---|
| Thiamine hydrochloride | 1,995 |
| Riboflavin | 10,000 |
| Niacine amide | 22,000 |
| Calcium D-pantothenate | 27,747 |
| Pyridoxolhydrochloride | 3,993 |
| Biotin | 250 |
| Folic acid | 1,090 |
| Cyanocobalamin | 5 |

In this context, after 30 hours of germination duration and subsequent thorough washing according to the microbiological VITAFAST® (microbiological assay for vitamins) method of R-Biopharm GmbH/Institut für Produktqualität Teltowkanalstralβe 2, D-12047 Berlin, the following vitamin values have been analyzed

| Sample number ifp | Coding | | | Total | Free | Bound |
|---|---|---|---|---|---|---|
| 07/2138 | L 259 M | Niacine | (mg/100 g) | 881 | 865 | 16 |
| | | Vitamin B1 (cal. as thiamine) | (mg/100 g) | 44 | 44 | 0 |
| | | Vitamin B2 (riboflavin) | (mg/100 g) | 195 | 174 | 21 |

After 45 hours of germination duration and subsequent thorough washing a significant increase in the portions of organically bound vitamins occurred, employing the same analysis method:

| Sample number ifp | Coding | | | Total | Free | Bound |
|---|---|---|---|---|---|---|
| 07/2139 | L 260 M | Niacine | (mg/100 g) | 959 | 910 | 49 |
| | | Vitamin B1 (cal. as thiamine) | (mg/100 g) | 52 | 50 | 2 |
| | | Vitamin B2 (Riboflavin) | (mg/100 g) | 224 | 185 | 39 |

The VITAFAST® analysis method was conducted according to Lindeke (HYGIENE Report 2 (2006):4-6).

The invention claimed is:

1. A method for producing germinated plants containing organically-bound vitamin B comprising:
    steeping germinative plant seeds in a vitamin-nutrient solution containing an effective amount of a vitamin B therein for 1 to 48 hours;
    removing the seeds from the vitamin-nutrient solution;
    exposing the seeds to a germination process, whereby the seeds are sprinkled with the vitamin-nutrient solution at least once a day for at least 2 days during the germination process so as to produce said germinated plants containing organically-bound vitamin B.

2. The method of claim 1, wherein the vitamin B is at least one of B1, B2, B3, B5, B6, B7, B9, or B12.

3. The method of claim 1, wherein the vitamin B is vitamin B1.

4. The method of claim 1, wherein the vitamin B is vitamin B2.

5. The method of claim 1, wherein the vitamin B is vitamin B3.

6. The method of claim 1, wherein the vitamin B is vitamin B5.

7. The method of claim 1, wherein the vitamin B is vitamin B6.

8. The method of claim 1, wherein the vitamin B is vitamin B7.

9. The method of claim 1, wherein the vitamin B is vitamin B9.

10. The method of claim 1, wherein the vitamin B is vitamin B12.

11. The method of claim 1, wherein the plant seeds are soaked for 1 hour to 24 hours.

12. The method of claim 11, wherein the plant seeds are soaked for at most 16 hours.

13. The method of claim 1, wherein the mass ratio of the plant seeds to the vitamin-nutrient of the respective vitamin is 1:1 to 1:20.

14. The method of claim 13, wherein the mass ratio of the plant seeds to the vitamin-nutrient of the respective vitamin is 1:1 to 1:5.

15. The method of claim 1, wherein the plant seeds are steeped in the vitamin-nutrient solution under suitable conditions to provide greater than 0.01 mg of the respective vitamin per 100 grams of the plant seeds.

16. The method of claim 15, wherein the plant seeds are steeped in the vitamin-nutrient solution under suitable conditions to provide greater than 0.1 mg of the respective vitamin per 100 grams of the plant seeds.

17. The method of claim 16, wherein the plant seeds are steeped in the vitamin-nutrient solution under suitable conditions to provide greater than 1 mg of the respective vitamin per 100 grams of the plant seeds.

18. The method of claim 17, wherein the plant seeds are steeped in the vitamin-nutrient solution under suitable conditions to provide greater than 10 mg and less than 20 grams of the respective vitamin per 100 grams of the plant seeds.

19. The method of claim 18, wherein the plant seeds are steeped in the vitamin-nutrient solution under suitable conditions to provide greater than 10 mg and less than 5 grams of the respective vitamin per 100 grams of the plant seeds.

20. The method of claim 19, wherein the plant seeds are steeped in the vitamin-nutrient solution under suitable conditions to provide greater than 10 mg and less than 1 grams of the respective vitamin per 100 grams of the plant seeds.

21. The method of claim 1, wherein the solution is sprinkled on the seeds during the germination process over at least 4 days.

22. The method of claim 1, further comprising isolating organically bound vitamin B from the plant after soaking and sprinkling.

23. The method of claim 1, wherein the plant seeds are edible.

24. The method of claim 1, wherein the plant seeds are grass, vegetable, and/or cereal seeds.

25. The method of claim 1, wherein the plant seeds are azuki bean, aramanth, lucerne, cress, bean, watercress, buckwheat, pea, fenugreek, soya, barley, oat, millet, pumpkin, chickpea, cabbage, lentil, linseed, corn, rice, radish, rye, sesame, mustard, sun flower, wheat, and/or quinoa seeds.

26. The method of claim 1, wherein genrminated plants are further processed to produce a material suitable for use in a food supplement, dietary preparation, functional food, and/or veterinary product.

27. The method of claim 26, wherein the material is in a solid, semi-solid or liquid form.

28. The method of claim 26, wherein the material is in a gastric-juice-resistant form.

* * * * *

UNITED STATES PATENT AND TRADEMARK OFFICE
CERTIFICATE OF CORRECTION

Page 1 of 1

PATENT NO. : 8,679,555 B2
APPLICATION NO. : 11/763974
DATED : March 25, 2014
INVENTOR(S) : Norbert Fuchs et al.

It is certified that error appears in the above-identified patent and that said Letters Patent is hereby corrected as shown below:

In the Claims

In claim 13, column 8, line 66, insert -- solution -- after "vitamin-nutrient".

In claim 14, column 9, line 2, insert -- solution -- after "vitamin-nutrient".

Signed and Sealed this
Third Day of June, 2014

Michelle K. Lee
*Deputy Director of the United States Patent and Trademark Office*